US010092350B2

(12) United States Patent
Rothweiler et al.

(10) Patent No.: US 10,092,350 B2
(45) Date of Patent: *Oct. 9, 2018

(54) ELECTROSURGICAL INSTRUMENT AND JAW PART THEREFOR

(71) Applicant: Aesculap AG, Tuttlingen (DE)

(72) Inventors: Christoph Rothweiler, Donaueschingen (DE); Eugen Herner, Balingen (DE); Christian Huber, Muehlheim (DE)

(73) Assignee: Aesculap AG, Tuttlingen (DE)

( * ) Notice: Subject to any disclaimer, the term of this patent is extended or adjusted under 35 U.S.C. 154(b) by 1121 days.

This patent is subject to a terminal disclaimer.

(21) Appl. No.: 14/370,553

(22) PCT Filed: Dec. 27, 2012

(86) PCT No.: PCT/EP2012/076945
§ 371 (c)(1),
(2) Date: Jul. 3, 2014

(87) PCT Pub. No.: WO2013/102602
PCT Pub. Date: Jul. 11, 2013

(65) Prior Publication Data
US 2014/0371743 A1    Dec. 18, 2014

(30) Foreign Application Priority Data
Jan. 4, 2012    (DE) .................. 10 2012 100 040

(51) Int. Cl.
*A61B 18/14* (2006.01)
*A61B 18/00* (2006.01)
*A61B 90/00* (2016.01)

(52) U.S. Cl.
CPC ...... *A61B 18/1445* (2013.01); *A61B 18/1442* (2013.01); *A61B 2018/0016* (2013.01);
(Continued)

(58) Field of Classification Search
CPC .................. A61B 18/1445; A61B 18/1442
See application file for complete search history.

(56) References Cited

U.S. PATENT DOCUMENTS 3,920,021 A    11/1975  Hiltebrandt
4,427,014 A     1/1984  Bel et al.
(Continued)

FOREIGN PATENT DOCUMENTS

CN    201082191 Y    7/2008
CN    101378702 A    3/2009
(Continued)

OTHER PUBLICATIONS

International Search Report and Written Opinion for International Application No. PCT/EP2015/063284, dated Sep. 9, 2015, 7 pages.
(Continued)

*Primary Examiner* — Joseph Dietrich
(74) *Attorney, Agent, or Firm* — RatnerPrestia

(57) ABSTRACT

An electrosurgical instrument including a jaw part made up of mutually movable instrument legs which have facing sides on which one or more electrode areas are arranged/formed in each case, the movement of the instrument legs relative to each other being able to be limited by at least one first spacer acting on proximal end portions of the instrument legs and at least one second spacer acting on distal end portions of the instrument legs. At least one of the spacers on at least one electrode is manufactured from an electrically conductive material and is connected to the electrode in electroconductive fashion. Furthermore, the spacer cooperates with a local spacer abutment surface which is made of a non-conductive material and arranged in electrically insulating manner on at least one opposing electrode.

15 Claims, 13 Drawing Sheets

(52) U.S. Cl.
CPC .............. *A61B 2018/00083* (2013.01); *A61B 2018/00494* (2013.01); *A61B 2090/033* (2016.02)

(56) References Cited

U.S. PATENT DOCUMENTS

| | | | |
|---|---|---|---|
| 5,222,973 | A | 6/1993 | Sharpe et al. |
| 5,258,006 | A | 11/1993 | Rydell et al. |
| 5,891,142 | A | 4/1999 | Eggers |
| 6,123,701 | A | 9/2000 | Nezhat |
| 6,190,399 | B1 | 2/2001 | Palmer et al. |
| 6,770,072 | B1 | 8/2004 | Truckai et al. |
| 6,802,843 | B2 | 10/2004 | Truckai et al. |
| 7,306,599 | B2 | 12/2007 | Karasawa et al. |
| 8,915,913 | B2 | 12/2014 | Fischer et al. |
| 2003/0014053 | A1 | 1/2003 | Nguyen |
| 2004/0019352 | A1 | 1/2004 | Kidooka |
| 2004/0122423 | A1 | 6/2004 | Dycus et al. |
| 2004/0162557 | A1 | 8/2004 | Tetzlaff |
| 2004/0249374 | A1 | 12/2004 | Tetzlaff |
| 2005/0107784 | A1 | 5/2005 | Moses |
| 2006/0217709 | A1 | 9/2006 | Couture et al. |
| 2006/0271038 | A1 | 11/2006 | Johnson |
| 2008/0015567 | A1 | 1/2008 | Kimura |
| 2008/0045944 | A1 | 2/2008 | Fischer |
| 2008/0056944 | A1 | 3/2008 | Nakamura |
| 2008/0215048 | A1 | 9/2008 | Hafner |
| 2010/0016857 | A1 | 1/2010 | McKenna |
| 2010/0023043 | A1 | 1/2010 | Houser |
| 2010/0057084 | A1 | 3/2010 | Hanna |
| 2010/0082047 | A1 | 4/2010 | Cosgrove et al. |
| 2010/0204698 | A1 | 8/2010 | Chapman |
| 2011/0082494 | A1 | 4/2011 | Kerr |
| 2011/0184404 | A1 | 7/2011 | Walberg |
| 2012/0083784 | A1 | 4/2012 | Davison |
| 2012/0101501 | A1 | 4/2012 | Nishimura et al. |
| 2012/0150167 | A1 | 6/2012 | Fischer |
| 2012/0271346 | A1 | 10/2012 | Townsend |
| 2013/0274741 | A1 | 10/2013 | Marczyk |
| 2014/0371743 | A1 | 12/2014 | Rothweiler |
| 2015/0216544 | A1 | 8/2015 | Banfalvi |
| 2015/0257819 | A1 | 9/2015 | Dycus |
| 2016/0157930 | A1 | 6/2016 | Heard |

FOREIGN PATENT DOCUMENTS

| | | |
|---|---|---|
| CN | 100544681 | 9/2009 |
| CN | 101522127 | 9/2009 |
| DE | 202004009427 U1 | 8/2004 |
| DE | 102004031141 A1 | 1/2006 |
| DE | 69925854 | 5/2006 |
| DE | 202006016837 U1 | 1/2007 |
| DE | 102006042985 A1 | 4/2007 |
| DE | 10200705359 | 6/2009 |
| DE | 102008008309 A1 | 8/2009 |
| DE | 102008018614 | 10/2009 |
| DE | 102009037614 | 2/2011 |
| DE | 202012100017 U1 | 3/2012 |
| DE | 102012100040 | 7/2013 |
| EP | 1372507 | 1/2004 |
| EP | 1123058 | 12/2005 |
| EP | 1747762 A2 | 1/2007 |
| EP | 1878400 A1 | 1/2008 |
| EP | 1952777 A1 | 8/2008 |
| EP | 1656901 B1 | 9/2009 |
| EP | 2165662 | 3/2010 |
| GB | 1461810 | 1/1977 |
| JP | 2000102545 | 4/2000 |
| JP | 2002528167 | 9/2002 |
| JP | 2004524923 | 8/2004 |
| JP | 2004532676 | 10/2004 |
| JP | 2006006942 | 1/2006 |
| JP | 2006528909 | 12/2006 |
| JP | 2007319683 | 12/2007 |
| JP | 2008018226 | 1/2008 |
| JP | 2009509706 | 3/2009 |
| JP | 2009297503 | 12/2009 |
| JP | 2010042248 | 2/2010 |
| JP | 2010051802 | 3/2010 |
| JP | 2010253278 | 11/2010 |
| WO | 0024331 | 5/2000 |
| WO | 2002080796 | 10/2002 |
| WO | 2002080797 | 10/2002 |
| WO | 2004103156 | 12/2004 |
| WO | 2011018153 | 2/2011 |
| WO | 2011097469 | 8/2011 |
| WO | 2013102602 | 7/2013 |
| WO | 2015197395 | 12/2015 |

OTHER PUBLICATIONS

German Search Report for German Application No. 10 2014 108 914.6, dated Mar. 10, 2015, 12 pages.
Japanese Office Action dated Aug. 24, 2016 for Japanese Application No. 2014-530246, including English translation, 9 pages.
Chinese Office Action dated Oct. 29, 2015 for Chinese Application No. 201280045066.1 with translation, 21 pages.
German Search Report issued in related German Application No. 10 2011 053 682.5, dated May 18, 2012, 3 pages.
International Search Report issued in related International Application No. PCT/EP2012/068158, dated Nov. 26, 2012, 3 pages.
Japanese Office Action for Japanese Application No. 2014-556987, dated Dec. 13, 2016 with translation, 5 pages.
German Search Report for German Application No. 10 2012 101 257.1, dated Nov. 28, 2012 with partial translation, 5 pages.
International Search Report and Written Opinion for International Application No. PCT/EP2013/052329, dated May 8, 2013, 13 pages.
Chinese Office Actioin dated Jan. 4, 2016 for Chinese Application No. 201380011277.8 with translation, 12 pages.
JP Office Action with English translation for Application No. 2014-550685, dated Nov. 22, 2016, 7 pages.
European Office Action for European Application No. 13 703 781.8, dated Apr. 28, 2017 with translation, 8 pages.
European Office Action for European Application No. 12 813 879.9, dated May 2, 2017 with translation, 8 pages.
Notice of Allowance for U.S. Appl. No. 14/377,352, dated May 8, 2017, 23 pages.
German Search issued in related German Application No. 10 2012 100 040.9, dated Aug. 28, 2012.
International Search Report and Written Opinion issued in related International Application No. PCT/EP2012/076945, dated Aug. 30, 2013.
Notice of Allowance for U.S. Appl. No. 14/377,352, dated Sep. 13, 2017, 12 pages.

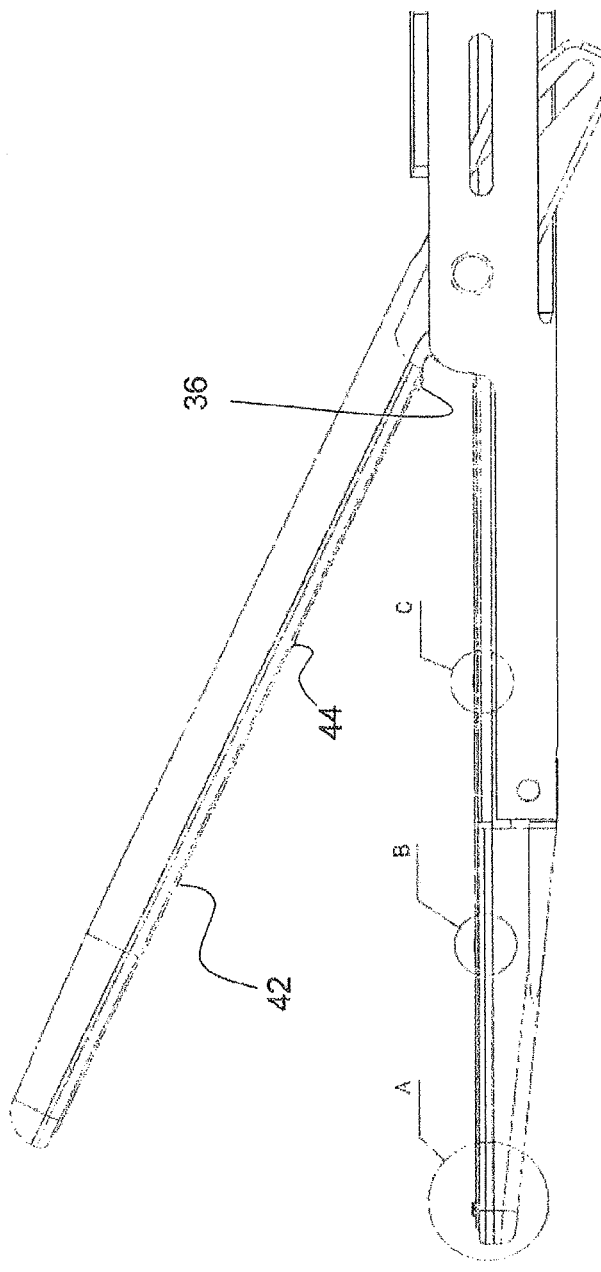
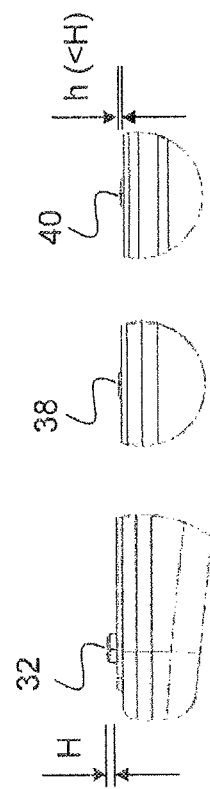
Fig. 9
Fig. 10A  Fig. 10B  Fig. 10C

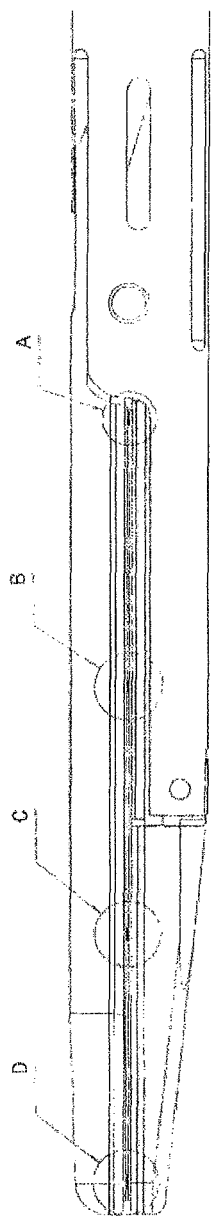
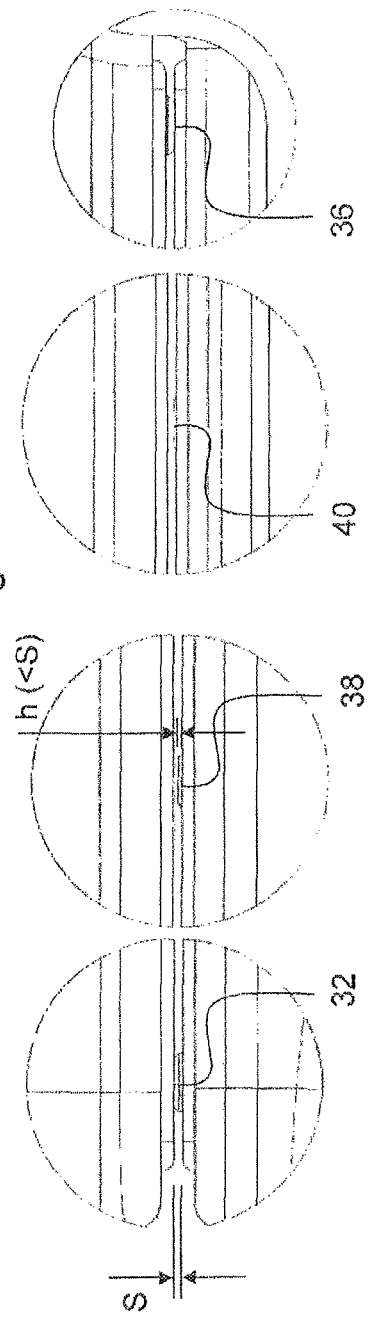
Fig. 11
Fig. 12A
Fig. 12B
Fig. 12C
Fig. 12D

ELECTROSURGICAL INSTRUMENT AND JAW PART THEREFOR

CROSS-REFERENCE TO RELATED APPLICATIONS

This application is the U.S. National Phase patent application of International PCT Application No. PCT/EP2012/076945, filed Dec. 27, 2012, which claims the benefit of priority of German Application No. 10 2012 100 040.9, filed Jan. 4, 2012, the contents of both applications being incorporated by reference herein in their entirety.

FIELD OF THE INVENTION

The present invention relates to an electrosurgical instrument, in particular for laparoscopic operations.

BACKGROUND OF THE INVENTION

Following the surgical removal of a hollow vessel portion, e.g. with an intestinal resection due to a tumor having affected a bowel section, the two hollow vessel portions have to be reconnected at their opened ends in such a manner that a continuous pathway is produced. This is referred to as end-to-end anastomosis. As a standard, the two opened ends are reattached to each other with clip suturing devices.

In particular with operations on the small and large intestines, leaky suture connections (suture insufficiency) occur from time to time, which are associated with a serious progress of disease and a high mortality rate, too.

An alternative to stitching the hollow vessel portions is thermofusion technology (TFT). Thermofusion by means of high frequency technology (HF) is based on the denaturation of proteins which are contained in many tissue types. This allows to weld collagen-containing tissue. During the welding process, the tissue is heated up to temperatures above the protein denaturation temperature, and together with the intra- and extracellular matrix is converted into a gel-like state. After compression of the tissue faces, the liquefied tissue cools down to a fused mass, effecting a reliable connection of the tissue.

For the purpose of welding the hollow vessel portions, the tissue grasped between two clamping jaws is exposed to electrical current which flows between electrodes provided on the two clamping jaws.

For preventing the sealing or welding from breaking down, the parameters acting on the tissue have to be detected and controlled. In order to ensure this, a precise control of temperature, pressure, tissue impedance, distance and position is required.

It is desirable to realize a uniform treatment of the tissue which is held between the clamping jaws, so that all regions are reliably reached and no region is exposed to an excessively high current. To this end, it has to be ensured that the HF electrodes are uniformly spaced from each other and aligned so as to be parallel to each other.

The prior art does not disclose any instruments of suitable size for being used for the above-mentioned hollow vessels and tissue types. Coagulation instruments of smaller size, as shown e.g. in EP 1 747 762 A2, exhibit a nonparallel alignment of the HF electrodes during closing the clamping jaws, which is due to the construction.

The distance between the electrodes can be maintained by spacers mounted on the clamping jaws. If, however, a larger number of spacers is provided on the clamping jaws, as is shown e.g. in EP 1 656 901 B1, EP1 952 777 A1, EP 1 372 507 A1 or US 2004/122423 A1, it is inevitable that the spacers perforate the tissue to be treated, as the tissue is compressed under the spacers with closed clamping jaws in such a manner that permanent damages on the tissue will occur. This has negative effects on the result of the sealing process.

If the contact pressure of the clamping jaws is reduced in order to avoid perforation of the tissue, and the tissue is only clamped underneath the spacers, this will result in an angular deflection of the clamping jaws.

As the spacers are further made from an electrically non-conductive material for avoiding a short-circuit between the HF electrodes, a so-called coagulation shade develops in the vicinity of said spacers, which means that the tissue portions are encapsulated in the vicinity of or under the spacers, hence are not supplied with electrical current or only to an insufficient extent, and an unsatisfactory welding of the vessel portions will be produced. Furthermore, it has turned out that electrically insulating spacers of this type may readily flake off, in particular in case they are attached to the electrode e.g. by gluing, with the risk that they may find their way into the patient body possibly even unnoticed. In addition to that, the predefined electrode spacing is not ensured any more.

Against this background, the present invention is based on the object to provide an instrument which improves, by means of thermofusion technology, the result of an end-to-end anastomosis of hollow vessels such as small and large intestines or, in general, improves the result with tissue connections, ensures in particular a parallel alignment of the HF electrodes without any damage on the tissue, and has an improved functional reliability.

SUMMARY OF THE INVENTION

The object is achieved with a generic medical instrument comprising a jaw part made up of mutually movable instrument legs or branches which have facing sides on which one or more electrode surfaces are arranged/formed in each case, the movement of the instrument legs or branches relative to each other being able to be limited by at least one first spacer acting on proximal end portions of the instrument legs or branches and at least one second spacer acting on distal end portions of the instrument legs or branches, characterized in that at least one of the spacers on at least one electrode is manufactured from an electrically conductive material and is connected to the electrode in electroconductive fashion, and cooperates with a local spacer abutment surface which is made of a non-conductive material and arranged in electrically insulating manner on at least one opposing electrode, wherein the spacer abutment surface comprises a concavity which points toward the spacer or is recessed with respect to the electrode area.

The present invention is based on the new knowledge briefly indicated above, which says that spacers which are immediately arranged on the electrode areas or fixed thereon and necessarily must be made hitherto from an electrically non-conductive material, locally limit/impede the flow of electrical current into the clamped tissue, so that a continuous tissue weld seam is not ensured. In order to reduce these negative effects, it would be basically possible to implement the spacers as small as possible, e.g. with the shape of a mandrel or needle. However, it has turned out that spacers formed in such a way do not withstand the clamping forces between the legs and hence are not able to stably maintain the leg spacing in the closed position. What is more, there is the risk that such non-conductive, nub-shaped protrusions can easily break off in use, and then remain unnoticed in the tissue of a patient for instance during an operation. For this reason, the present invention basically suggests to manufacture the preferably nub-shaped spacers made of an electrically conductive material and directly arranged on the electrode areas or fixed thereon e.g. such that they are formed integrally with or soldered/welded to the corresponding electrode, and instead to provide non-conductive spacer abutment surfaces on the respectively opposing electrode, on which the electrically conductive spacers will come to rest. As the electrically non-conductive spacer abutment surfaces, for instance in the form of glued, applied, inserted or poured-in pads/platelets/pins are substantially level with the electrode area, i.e. have none or only a small protruding portion with respect to the corresponding electrode area, they can not be detached/torn off from the electrode area or only with difficulty. Accordingly, each of the spacer abutment surfaces can be realized with a smaller size regarding the areal dimensions compared to electrically non-conductive spacers known hitherto, as the spacer abutment surfaces do not have to introduce any shear forces into the electrode which is due to the small or missing protruding portion. The spacers themselves may consist of a material such as metal which withstands high shear forces, so that they can be dimensioned in small size, too. As a whole, this contributes to avoid coagulation shadows and at the same time to improve the functional reliability.

It is advantageous if the spacer abutment surfaces in the form of pads or pins are inserted in corresponding indentations or recesses (depressions) on the surface of the respective electrode, so that they define a surface which is substantially level with the electrode (without any protruding portion). It is also advantageous if each spacer abutment surface is shaped in the form of a pin comprising a flat plate portion with an underside to which a mandrel-like protrusion is attached. Said mandrel-like protrusion is fitted in a corresponding hole in the electrode and brings about an even stronger fit/grip of the spacer abutment surface in the electrode recess.

In addition to the measures described above, provision can be made to keep the number of electrodes fixed on the respective electrode area and hence the number of inserted, non-conductive spacer abutment surfaces as small as possible, in order to reduce the effects of coagulation shadows.

Accordingly, a coagulation instrument of the invention for surgical purposes and of the relevant type specifically comprises mutually movable instrument legs (preferably in the nature of scissors or jaws) each comprising one or more electrode areas on the respectively facing leg sides, between which the tissue can be clamped and treated in electrothermal way. The movement of the instrument legs relative to each other is limited by at least one first spacer acting on proximal end portions of the instrument legs and consisting of an electrically conductive material and a pad-shaped or pin-shaped spacer abutment surface of an electrically non-conductive material, and by at least one second spacer acting on distal end portions of the instrument legs and preferably made from an electrically non-conductive material. According to the invention, not more than one protrusion made of an electrically conductive material and acting as a spacer is preferably integrally provided with or formed on the electrode e.g. by embossing or stamping, or fixed thereon for instance by welding or soldering, on each electrode area. On the opposite electrode, the pad or pin made of an electrically non-conductive material is inserted in a corresponding indentation or attached/glued thereto, to define the spacer abutment surface for the one protrusion.

By providing a spacer and an associated spacer abutment surface, which act on the proximal end portions of the instrument legs, and by providing a preferably electrically non-conductive spacer or spacer abutment surface combination, which acts on the distal end portions of the instrument legs, it is generally ensured that the electrodes have a predetermined distance from each other over their entire length and hence extend preferably parallel to each other. Due to the large distance of the spacers and their points of attack in the longitudinal direction of the legs, the parallelism of the instrument legs and the electrode areas mounted thereon is improved, as possible manufacturing tolerances during forming the spacers only have small effects on the parallelism of the legs in the closed position. Due to the substantially uniform electrode spacing, which can be adjusted in this way, between the two legs in the closed position, a uniform penetration of the tissue with HF energy and an even current density in the tissue are achieved.

As already mentioned at the outset, an excessively high number of spacers, in particular if they are immediately arranged/fixed on the electrode areas, would result in the tissue being damaged too much. Further, a corresponding number of coagulation shadows would be produced.

According to the invention, damaging of the tissue and an inhomogenous penetration of the tissue with HF energy is further minimized in that not more than one spacer is applied on each electrode area, which also means that selected electrode areas do not comprise any spacer in the form of a (nub-shaped) protrusion (of an electrically conductive material) fixed or formed thereon, and the spacer(s) instead is/are realized at another position (i.e. outside the electrode areas) on the instrument leg or with different means (e.g. not in fixed but in loose manner), whereby the tissue is damaged to a lesser extent and the development of coagulation shadows is further reduced.

Thus, the coagulation clamp according to the invention and its instrument legs according to the invention provide an optimum tradeoff between the best parallel alignment of the HF electrodes in the closed position of the legs, on the one hand, and a homogenous tissue fusion with smallest tissue damage, on the other hand. This is why tissue damages caused by the spacers as a result of an excessive application of force on the clamped tissue are prevented and a reliable fusion of the individual tissue components is ensured by a consistent relationship of forces, the parallel arrangement of the electrodes, the clearly defined distance of the electrodes and the homogenous distribution of the electrical current in the tissue along the electrodes. In addition, the particular arrangement of at least a subset of spacers outside the electrode areas avoids short-circuits between the electrodes and leaks on the sealed tissue layers, even if these special spacers consist of a conductive material. This results in consistent prerequisites for HF surgery in particular regarding the impedance of the tissue, so that the quality of the sealed tissue zones can be better monitored as seen from the viewpoint of electrical control.

According to another or additional aspect of the invention, the spacers (all of them) are arranged exclusively outside a region provided for tissue treatment, preferably only at the proximal and distal ends of the legs. If the spacers act only on the proximal and distal end portions of the instrument legs and if the middle region of the instrument legs, which normally represents the actual or substantial treatment zone of the tissue, is not provided with spacers, any damage of the tissue by the spacers and the coagulation shadows caused by the spacers are avoided in this main sector.

According to a further or other aspect of the present invention, a spacer, which acts for instance on the proximal end portions of the instrument legs, is a spacer module which is formed to be separate from the instrument legs and comprises at least one electrically non-conductive material tongue which is clamped between the instrument legs in their closed position. Accordingly, the height of the material tongue corresponds to a predetermined parallel distance to be set between the instrument legs.

A separate spacer module of this type has several advantages. On the one hand, it can be manufactured in easy way and independently from the respective instrument legs or the coagulation clamp, for which it is to be used. On the other hand, it can be replaced at any time, whether for reasons of wear and tear or for replacing it by another spacer module comprising thicker or thinner material tongues. This allows to vary the distance of the instrument legs in the closed position. Consequently, the physical separation of the instrument legs and the spacers has the advantage that the same spacer module can be provided for different instrument legs or different spacer modules can be provided for the same instrument legs. In the case of a material tongue which is loosely retained as well as clamped between the electrode areas in the closed position of the legs, the coagulation shadow effect will be smaller than with a spacer which is fixed on the electrode areas, even if the spacer consists of an electrically conductive material and cooperates with a spacer abutment surface made of an electrically non-conductive material.

The spacer module may comprise several material tongues (of a non-conductive material) which are spaced from each other laterally or in the transverse direction of the legs, for instance for the purpose of leaving an electrical cutting portion blank which is provided between two coagulation electrode faces.

For opening and closing the instrument legs, at least one of the instrument legs can be pivotally supported e.g. on an instrument shaft or on the opposing leg and can be actuated via a manipulation mechanism (supported in the instrument shaft and/or in the handle piece), to move the instrument legs toward to and apart from each other. The spacer module can be rotatably supported in a swivel joint of the operable (supported) instrument leg; in particular, it may be encompassed here in the nature of a housing by joint portions of the operable instrument leg.

By integrating the spacer module in the swivel joint of one or both instrument legs, it is not only housed in the interior of the instrument or jaw part in a space-saving manner, but exerts its spacer function by its own without any additional actuation by the surgeon, when the instrument legs are being closed.

As an alternative or in addition to the separate spacer module as mentioned above, at least one of the instrument legs, preferably the pivotable leg, may comprise a rotation limiter pin which is guided in a slot-type guide on the side of the respective other leg, the cooperation between the rotation limiter pin and the slot-type guide establishing or simulating a sort of spacer, in particular the spacer acting on the proximal end portions of the instrument legs, and the instrument legs having a predetermined minimum distance relative to each other if the at least one rotation limiter pin reaches an end portion of the slot-type guide. If both instrument legs are supported in pivotable manner or so as to be able to be moved in any other way (e.g. shiftable), the degree of freedom of both instrument legs can be limited in each case by a rotation limiter pin which is guided in a respective slot-type guide.

This solution especially has the advantage that the spacer, at least in the proximal end portion of the legs, can be arranged completely outside the clamping area of the instrument legs, i.e. outside the tissue treatment zone (electrode areas) and there will be no contact between the spacer and the tissue to be treated. This allows to reliably prevent the tissue from being damaged.

A spacer, for instance the spacer acting on the distal end portions of the instrument legs, may be formed by a (nub-shaped) protrusion arranged between two electrode areas and pointing toward the other instrument leg. If the spacer is hence not arranged on the electrode areas, but beside or between them, there will be no coagulation shadows in that region, in particular because the spacer(s) does not/do not have to be made from an insulating material. If the spacer is arranged between the electrode areas, in particular if it is arranged on the central axis of one of the instrument legs and without any direct contact with the electrode areas, there will be no electrical short-circuit between the electrode areas. In addition, there will be no torsional load on the instrument legs, if these are pressed against each other in the closed position and kept apart from each other merely by the spacer. This allows to further reduce the number of the spacers on the whole.

As an alternative or in addition, one or more spacers, in particular those spacers which act on the proximal and/or distal end portions of the instrument legs, can be formed by only one protrusion immediately provided/fixed on an electrode area or by several protrusions immediately provided/fixed on different electrode areas. In this way, a parallel alignment of the electrodes in the longitudinal direction is ensured, on the one hand, and the number of the spacers which are fixed on the electrode areas is kept small, on the other hand, whereby an optimum treatment, in particular a homogenous fusion of the tissue is made possible.

Especially with particularly long instrument legs or such ones which are centrally supported in the nature of a rocker e.g. at the end of an instrument shaft, it has to be guaranteed that the electrode areas maintain the desired distance in the middle region; said distance must not decrease due to bending stress (in particular if the two legs are pressed against each other at their end portions). This is why, in addition to the first and second spacers acting on the proximal and distal end portions of the instrument legs, respectively, at least one third spacer of the invention may be provided, which acts on middle portions of the instrument legs, with the at least three spacers basically being arranged such that not more than one spacer is fixed/formed on each electrode area of a leg. In the specific case, the third spacer would be arranged on another electrode area than the first and/or second spacer(s) or between the electrode areas. Even if the centrally acting spacer can come into contact with the tissue here, the specific arrangement and the number of the spacers according to above definition ensure that the effects on the tissue are kept at a minimum, on the one hand, and a uniform distance between the electrodes is ensured over the entire length of the HF electrodes and the legs, on the other hand.

Between the proximal end portion and the distal end portion of at least one instrument leg, one or more (nub-shaped) ridges may be formed which point toward the other instrument leg and have a height which is smaller than the height of the spacers, in particular amounts to 10% to 75% of the height of the spacers.

Due to the ridges or teeth which are additionally arranged on the instrument leg, in particular on one or both electrode areas of one or both legs, the tissue can be gripped more reliably, in order to prevent the tissue to be treated or the tissue portions to be treated from slipping out of the instrument legs, before they have been fused to each other.

As this ridge is smaller than the minimum distance of the two instrument legs which is defined by the spacer in the closed position, e.g. 10% to 75% of the distance, these will never come to rest against the opposing instrument leg. This is why the tissue between the ridge and the opposing instrument leg is not perforated and hence not permanently damaged. Further, these ridges do also not cause any coagulation shadows, as the tissue clamped between the ridge and the opposing instrument leg is not covered to a substantial extent. In this way, the coagulation shadows are prevented, which occur when conventional instruments are used. As these ridges do not come into contact with the opposing instrument leg anyway, they too may be made of an electrically conductive material; in this case, opposing pads/pins of electrically non-conductive material may be dispensed with. It is possible, of course, to provide several of such ridges for each electrode area. They can be arranged at regular intervals.

As has already been indicated in part above, the instrument legs may comprise two or more opposing, e.g. parallel pairs of electrode areas, where the protrusions and/or ridges are formed on different pairs of electrode areas. Especially the instrument leg which cannot be operated, may be centrally supported e.g. on the end portion of an instrument shaft so as to be able to pivot to a certain degree in the nature of a rocker, to be able to equalize any angular deviations with respect to the operable instrument leg in the closed position. It goes without saying that the coagulation clamp or the jaw part may comprise two legs which can be separated from each other or translatorily shifted with respect to each other.

It is to be noted that all the aspects and features mentioned above can be combined individually and also in grouped fashion.

BRIEF DESCRIPTION OF THE DRAWINGS

FIG. 9 shows a side view of the two instrument legs of FIG. 8 in the open position;

FIGS. 10A, 10B and 10C shows detail views A, B and C of FIG. 9;

FIG. 11 shows a side view of the two instrument legs of FIG. 8 in closed position;

FIGS. 12A, 12B, 12C and 12D show detail views A, B, C and D of FIG. 11;

DETAILED DESCRIPTION OF THE PREFERRED EMBODIMENTS

Figure 1:
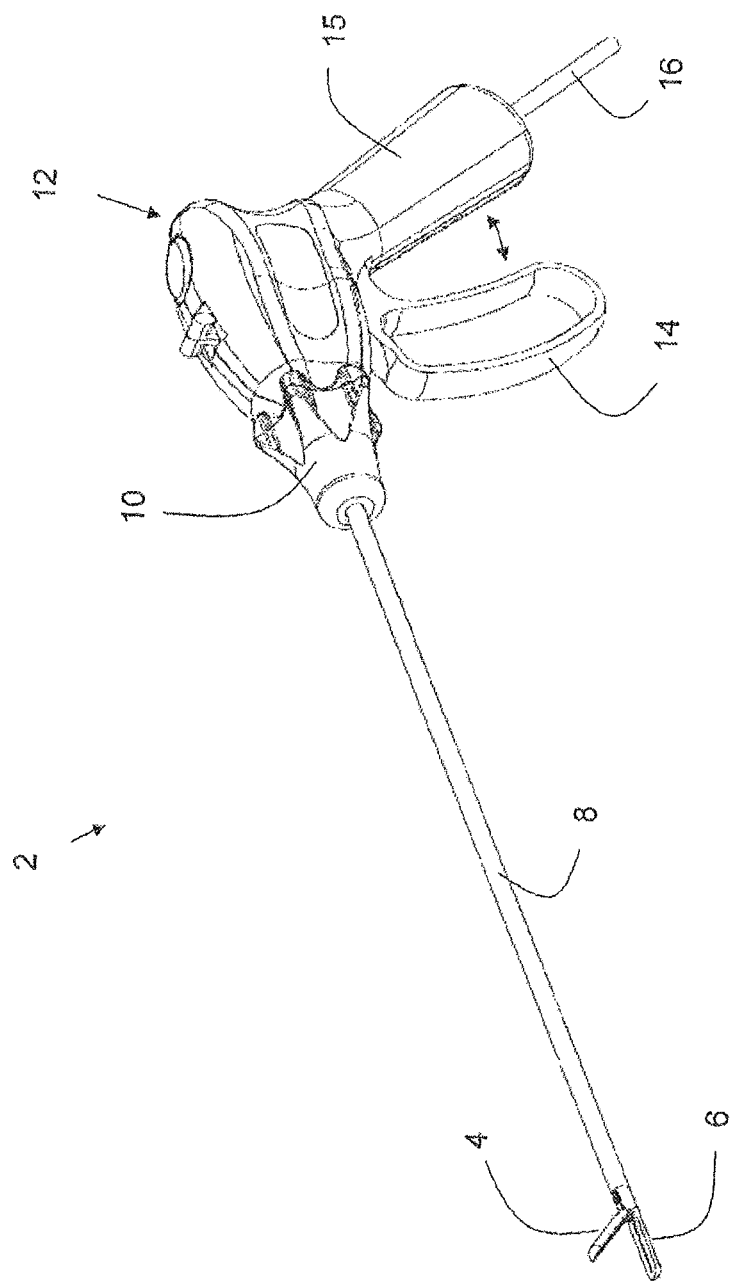
FIG. 1 shows an electrosurgical instrument according to a first embodiment of the invention.

FIG. 1 shows a perspective view of a laparoscopic electrosurgical instrument 2 in open position according to a first embodiment of the invention, comprising a jaw part consisting of a pair of instrument legs 4 and 6, which move relative to each other preferably in the manner of scissors or tongs, and are arranged on the distal end of an instrument shaft 8 which for its part is rotatably fastened to a handle piece or manipulation part 12 via a manually operable shaft rotation device 10. The shaft rotation device 10 allows to rotate the shaft 8 (and the instrument legs 4 and 6 arranged thereon) relative to the manipulation part 12 about the longitudinal axis of the shaft. The manipulation part 12 comprises a manually operable handle or trigger guard 14 which is able to move in pivoting manner relative to a handle or pistol grip 15 firmly connected to the manipulation part 12. The instrument legs 4, 6 or at least one manually operable instrument leg 4 are/is in operative connection with the handle 14 via an operation mechanism (not shown in further detail), e.g. a cable pull or a push rod within the instrument shaft 8, and can be shifted from an open position to a closed position (and vice versa) preferably continuously by manually operating the handle 14. By means of a line (which is only shown in part) or electric cabling 16, the manipulation part 12 is connected to a (not shown) HF energy source, in order to be able to apply HF voltage for the electrothermal treatment of tissue between the instrument legs 4 and 6.

Regarding the basic mode of operation and the mechanical structure of the instrument 2, in particular with respect to the operation mechanism, reference is made for instance to the published document WO 2011/097469 A2.

Figures 2, 3:
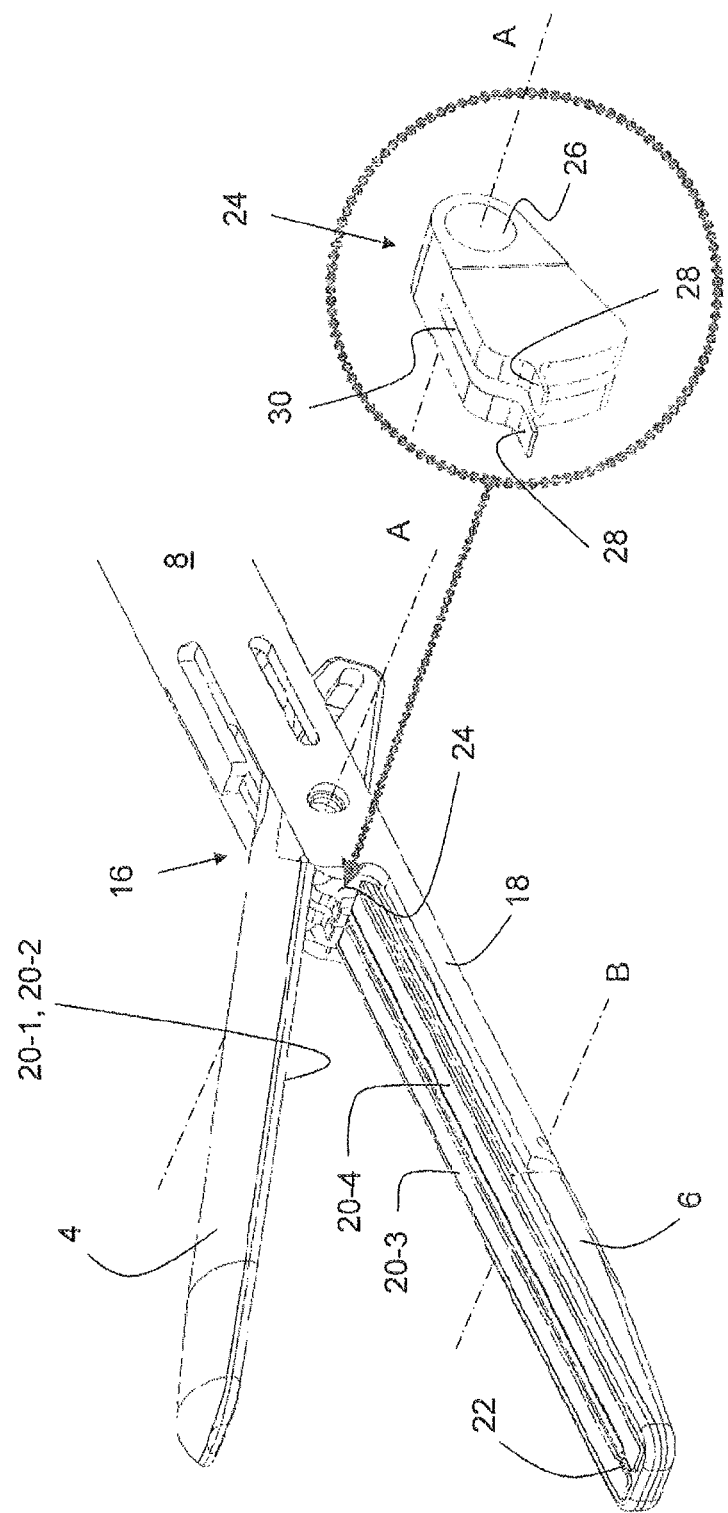
FIG. 2 shows a perspective view of two (scissor-type) mutually pivotable instrument legs of the electrosurgical instrument according to the first embodiment of the invention.
FIG. 3 shows an enlarged view of a spacer module according to the first embodiment of the invention.
Figure 4:
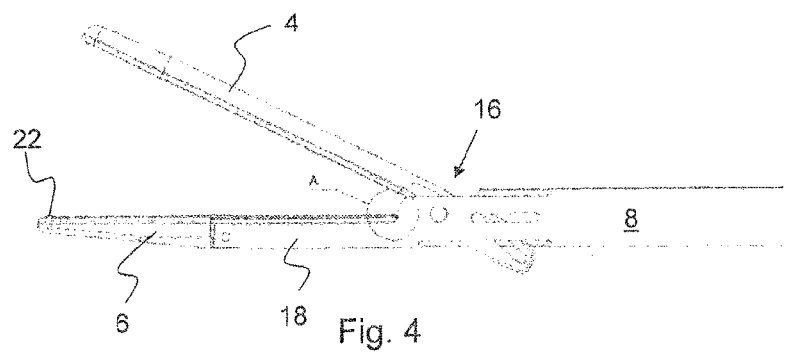
FIG. 4 shows a side view of the two instrument legs of FIG. 2 in open position.

FIGS. 2 and 4 show a detail view of the distal end of the shaft 8 or the jaw part connected to the shaft 8 together with the instrument legs 4 and 6 in the open position. The first instrument leg 4, which is the upper one according to FIG. 2 or 4, is supported by a proximal swivel joint or hinge 16 (see FIG. 4) on the distal end of the shaft 12 so as to be able to swivel about a transverse axis A. To this end, the distal shaft end or the jaw part connected thereto comprises a centrally formed through slot or longitudinal gap 17 extending along the shaft and comprising side flanges which are provided with one transverse hole each that are coaxially aligned with respect to each other and define the previously mentioned transverse axis A. The through slot 17 further has a slot width which allows to insert the first instrument leg 4 so as to be movable/pivotable therein. In the axial, distal prolongation (cantilever portion) of the through slot 17, the distal shaft end or jaw part forms a supporting protrusion or carrier 18 in the form of a half-shell or channel, which is opposite the rotatable upper instrument leg and comprises a transverse through-hole provided at its distal end portion and extending substantially parallel to the transverse axis A.

As seen in the longitudinal direction of the shaft, the second instrument leg 6 which is the lower one according to FIG. 2 or 4 is (axially) received in the shell-like supporting protrusion 18 only by a partial length portion and such that it projects beyond its remaining partial length portion axially over the supporting protrusion 18 in distal direction. Furthermore, the lower instrument leg 6 is pivotally articulated (in the type of a rocker) to the supporting protrusion 18 via the distal transverse through-hole. By means of a (not shown) spring mechanism (see WO 2011/097469 A2, inter alia), the front or distal rocker part of the lower instrument leg 6 is prestressed according to FIG. 4 toward the top or the upper instrument leg 4, whereby the lower leg 6, as seen in the longitudinal direction, encloses a smaller angle with the instrument shaft 8 or supporting protrusion 18; this is why the distal end portions of the two legs 4, 6 first come into clamping contact like forceps if the jaw part is folded or closed. This facilitates the gripping of tissue. The lower instrument leg 6 is supported on the portion or supporting protrusion 18 like a rocker to be able to pivot around axis B defined by the transverse through-hole only to such an extent that, in the closed condition, minor angular deviations between the upper and lower instrument legs 4 and 6 can be equalized, or a parallel alignment of both legs 4, 6 is achieved.

According to the present exemplary embodiment, each of the instrument legs 4 and 6 comprises preferably two electrodes or electrode areas 20 (20-1, 20-2, 20-3 and 20-4) which are spaced apart from each other in the transverse direction of the legs and extend substantially parallel in the longitudinal direction of the legs, and can be supplied with HF voltage. Accordingly, if there is any tissue between the instrument legs 4 and 6 in their closed position, the surgeon is able to coagulate, to sever or to weld it by means of the electrode areas 20. Further, a (not shown) special electrosurgical knife or an appropriate cutting device can be arranged between the electrode areas 20 so as to be electrically isolated from the electrode areas 20.

In order to avoid a short-circuit between the electrode areas 20 of the two instrument legs 4 and 6 and to ensure that a homogenous current flows through the tissue clamped between the electrode areas 20 over the entire length of the electrodes, the electrode areas 20 have to remain equally spaced also in the closed position. To this end, the instrument 2 comprises a preferably nub-shaped protrusion 22 at the distal end portion of the lower instrument leg 6 (and/or of the upper instrument leg 4) between the two electrode areas 20-3 and 20-4, which projects beyond the electrode areas 20-3 and 20-4 by a predetermined measure which corresponds to the desired distance between the electrode areas 20, and which comes into contact with the upper instrument leg 4 (and/or the lower instrument leg 6) during closing the jaw part and in this way acts as a spacer on the distal end portions of the two instrument legs 4 and 6.

According to this exemplary embodiment, the distance between the electrode areas 20 on the proximal end portions of the two instrument legs 4 and 6 is accomplished by a separate spacer module 24, i.e. is freely supported so as to be separate from the electrodes 20 and the legs 4, 6. In the present case, this spacer module 24 is a cam-shaped component comprising a proximal support portion (i.e. a cam portion comprising a transverse through-hole), which can be made to engage on the swivel joint (swivel pin) 16 and is able to freely rotate between the instrument legs 4 and 6 and hence around the swivel axis A. For reasons of space, the movable upper (and/or lower) leg 4 is/are hollowed in the present case at its/their proximal end portion(s) in the area of the swivel axis A in the longitudinal direction, whereby a sort of accommodation space or longitudinal groove is produced, whose dimensions are sufficient for receiving the spacer module 24 therein. This means that the spacer module 24 is received between two groove flanges of at least the one operable instrument leg 4 at least in the closed position of the jaw part.

FIG. 3 shows an enlarged perspective view of the spacer module 24 alone. As already indicated above, the module 24 has a sort of cam shape comprising the proximal support portion where the cam has such a cam thickness/height, that it can be inserted in the proximal longitudinal groove of the one leg 4 so as to be movable therein. Further, the transverse through-hole 26 is formed in the support portion of the module 24. On the distal outer transverse side of the module 24, remote from the support portion, there are two flat material tongues 28 formed so as to project radially with respect to the swivel axis A, whose respective flat sides face the legs 4, 6; their tongue thickness/height H corresponds to a minimum distance S (gap dimension) to be achieved between the opposing electrode areas 20-1 and 20-3 or 20-2 and 20-4 in the closed position of the legs 4, 6, and their lateral distance (in the transverse direction of the legs) and width correspond substantially to the parallel distance and the width of the electrode areas 20, so that the material tongues 28 come to rest on the electrode areas at least in part. An open longitudinal slit 30 is formed in the cam-shaped module 24 between the two material tongues 28 at the distal end of the module 24, which extends toward the support portion and ends immediately before the transverse hole 26. In this exemplary embodiment, the entire spacer module 24 or at least the material tongues 28 are made from an electrically non-conductive material.

Figure 5:
FIG. 5 shows a side view of the two instrument legs of FIG. 2 in closed position.
Figure 6A:
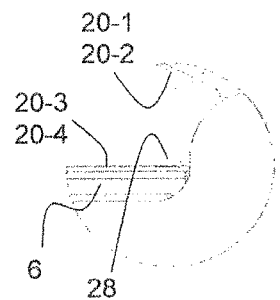
FIGS. 6A, 6B, 6C show detail views A, B and C of FIGS. 4 and 5.
Figure 6C:
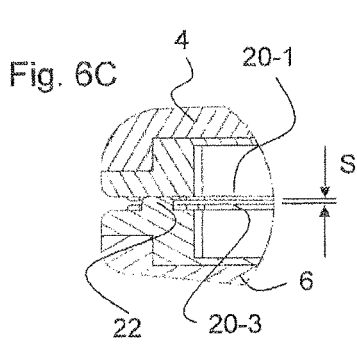
Figure 6B:
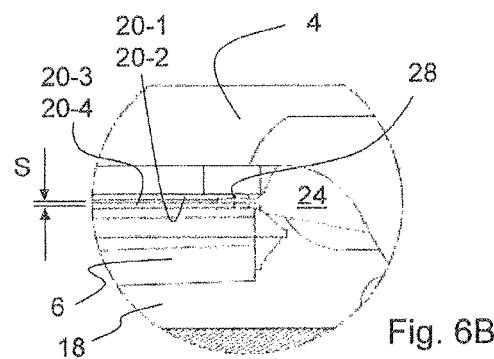

FIGS. 4 and 5 show a side view of the jaw part or of the instrument legs 4 and 6 in the open position and in the closed position, respectively. FIGS. 6A, 6B and 6C show detail views of the jaw part according to FIGS. 4 and 5.

It can be seen in FIG. 6A that the material tongues 28 of the spacer module 24 have loose contact on a proximal end portion of the electrode areas 20-3 and 20-4 of the lower instrument leg 4, if the jaw part is in the open position. If the instrument legs 4 and 6 are moved to the closed position (see FIG. 5), by actuating preferably the upper instrument leg 4, the material tongues 28 of the separate spacer module 24 are clamped (see FIG. 6B) between the proximal end portions of the electrode areas 20 of the two instrument legs 4 and 6, and the protrusion 22 on the distal end portion of the lower instrument leg 6 comes to rest on the distal end portion of the upper instrument leg 4. Thus, the proximal and distal end portions and hence the entire electrode areas 20 continue to be spaced by the predetermined gap dimension S and remain substantially parallel to each other.

As explained above, the (nub-shaped) protrusion 22 is arranged between the electrodes and thus makes a direct contact with the upper, operable leg 4 (and not with the upper electrode areas of the leg 4). Moreover, the proximal material tongues 24 are not directly fixed to the electrode areas, but only rest against them. Thus, the first embodiment does not involve a spacer which is immediately provided on one of the electrode areas 20 (in the sense of "fixed thereon"). This allows to reduce coagulation shade effects as against prior art.

Figure 7:
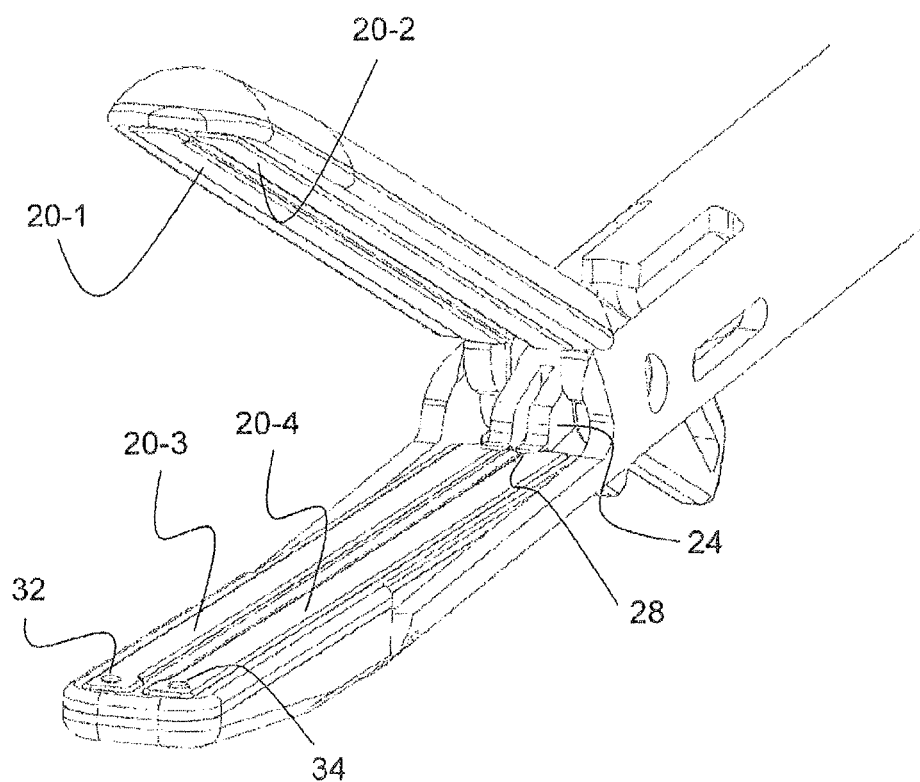
FIG. 7 shows a perspective view of two mutually pivotable instrument legs of an electrosurgical instrument according to a second embodiment of the invention.

FIG. 7 shows a second embodiment which differs from the laparoscopic electrosurgical instrument 2 of the first embodiment only in the arrangement of the distal spacer, which is why only the differences to the first exemplary embodiment are explained in the following.

In the second embodiment, two (nub-shaped) protrusions 32, 34 are immediately provided (i.e. firmly fixed) on the distal end portions of the electrode areas 20-3 and 20-4, instead of the protrusion 22 arranged between the electrode areas 20-3 and 20-4. In order to avoid a short-circuit between the electrode areas if these approach the electrode areas of the upper instrument leg 4 in the closed position, the protrusions 32, 34 are manufactured from an electrically conductive material and come to rest against a spacer abutment surface made of a non-conductive material which is provided on the respectively other of the opposing electrodes (exclusively) in the region of the respective protrusion (point-/pad-shaped). The protrusions 32, 34 may be applied by soldering or injection-molding or can be formed integrally (such as by embossing or stamping). The spacer abutment surface can be formed by injection-molding, spreading or filling in a hardening mass or by gluing or inserting an insulation platelet/pad/pin preferably on/in an indentation in the respective electrode, as will be explained in more detail below.

Figure 8:
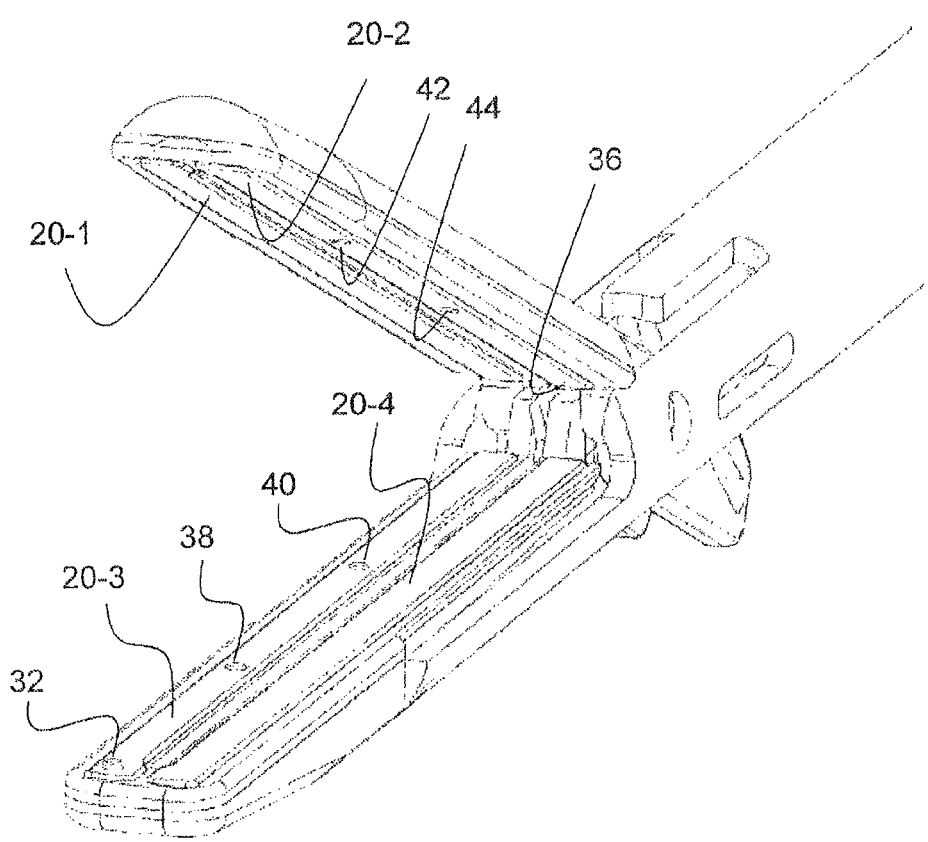
FIG. 8 shows a perspective view of two mutually pivotable instrument legs of an electrosurgical instrument according to a third embodiment of the invention.

FIG. 8 shows a perspective view of a laparoscopic electrosurgical instrument 2 according to a third embodiment, which differs from the first and second embodiments in that only one (nub-shaped) protrusion 32 is provided (fixed) on one (20-3) of the two electrode areas 20-3 and 20-4 at the distal portion of the lower (not operable) instrument leg or alternatively on the upper, operable instrument leg. Instead of the separate spacer module 24 which has been used hitherto, a (nub-shaped) protrusion 36 is arranged (fixed) on the proximal end portion on one (20-2) of the two electrode areas 20-1 and 20-2 of the upper instrument leg 4 or in corresponding manner alternatively on the lower leg. If the two instrument legs 4 and 6 are in the process of being closed, the protrusion 32 fixed on the lower electrode area 20-3 comes to rest on the upper electrode area 20-1, i.e. on the insulation platelet on the upper electrode, and the protrusion 36 which is fixed on the upper electrode area 20-2 comes to rest on the lower electrode area 20-4 or the insulation platelet on the lower electrode. In this way, each electrode area is provided with only one fixed protrusion at most, with two electrode areas not comprising any fixed protrusion at all.

It can be taken from FIG. 8, and in particular from the further FIGS. 9 to 12, that in addition to the protrusions 32 and 36 serving as spacers, two (or another number larger than zero) ridges 38 and 40 or 42 and 44 are arranged in the middle region of the instrument legs 4 and 6, for instance on the electrode areas 20-3 and 20-2. It can be seen in the enlarged views 9A, 9B and 9C, that the preferably nub-shaped ridges 38 and 40 have a smaller height than the protrusion 32 of said leg 6. Same applies to the ridges 42, 44 and the protrusion 36 on the upper instrument leg 4. If the instrument legs 4 and 6 are being closed, only the protrusions 32 and 36 will come to rest against the respectively opposing electrode area 20-1 and 20-4 (see FIGS. 11D and 11A), whereas the ridges 38, 40, 42, 44 continue to be spaced from the opposing electrode areas. Thus, the ridges 38, 40, 42, 44 do not act as spacers, but only as gripping elements, to prevent the tissue from slipping out of the legs between which it is clamped.

Figure 13:
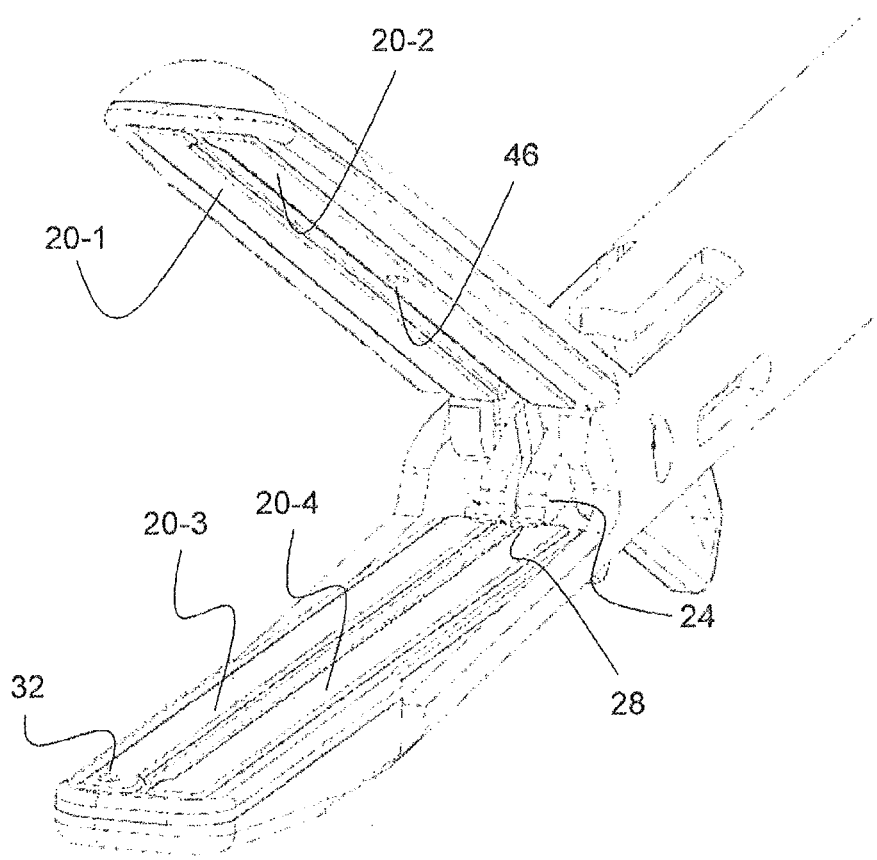
FIG. 13 shows a side view of two mutually pivotable instrument legs of an electrosurgical instrument according to a fourth embodiment of the invention.

FIG. 13 shows a fourth embodiment which differs from the laparoscopic electrosurgical instrument 2 of the first embodiment in the arrangement of the distal spacer, on the one hand, and comprises a third, centrally arranged spacer, on the other hand. Instead of being provided between the electrode areas 20-3 and 20-4, a (nub-shaped) protrusion 32 acting as a distal spacer is provided immediately (i.e. fixed) on the electrode area 20-3. The proximal spacer is again formed by the spacer module 24, as has already been described on the basis of the first exemplary embodiment. In addition, a centrally arranged (nub-shaped) protrusion 46 with the same height as the protrusion 32 and the material tongue(s) 28 is provided (fixed) on the electrode area 20-2. This additional middle protrusion counteracts a (convex) deflection of the legs and hence a central approach of the electrode areas.

Figure 14:
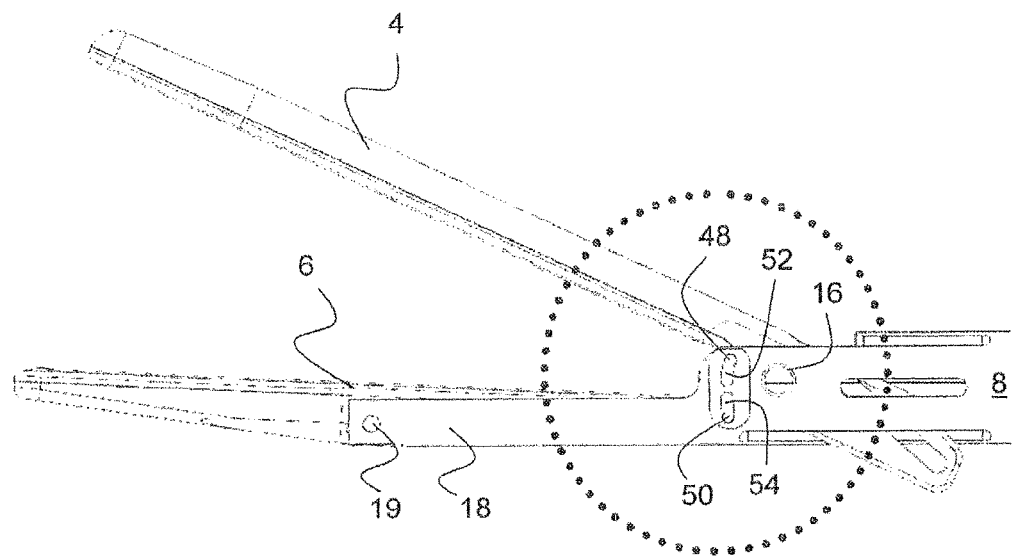
FIG. 14 shows a perspective view of two mutually pivotable instrument legs of the electrosurgical instrument according to the fourth embodiment of the invention.

FIG. 14 shows a fifth embodiment which differs from the laparoscopic electrosurgical instrument 2 of the first embodiment merely in the implementation of the spacer acting on the proximal portions of the instrument legs 4 and 6. Instead of a modular spacer 24, the instrument legs or at least the one operable leg have/has in this case their/its proximal portion(s) (end portions) provided with rotation limiter pins 48 and 50 which extend in transverse direction of the leg and are received in groove-shaped slot-type guides 52 and 54 on the respective other (preferably not actuated) leg or on the side walls of the shaft-sided longitudinal through-slot and are guided therein. The slot-type guides 52 and 54 limit the degree of freedom of the rotation limiter pins 48 and 50 and hence the pivoting range of the at least one instrument leg 4 (and/or 6). If the rotation limiter pins 48 and 50 reach the respective end of the slot-type guides 52 or 54, the instrument legs 4 and 6 have their predetermined and desired maximum opening and/or closing distance relative to each other. In this way, the cooperation of the rotation limiter pins 48 and 50 and the slot-type guides 52 and 54 serves as/simulates a proximal spacer in this fifth embodiment.

Figures 15, 16:
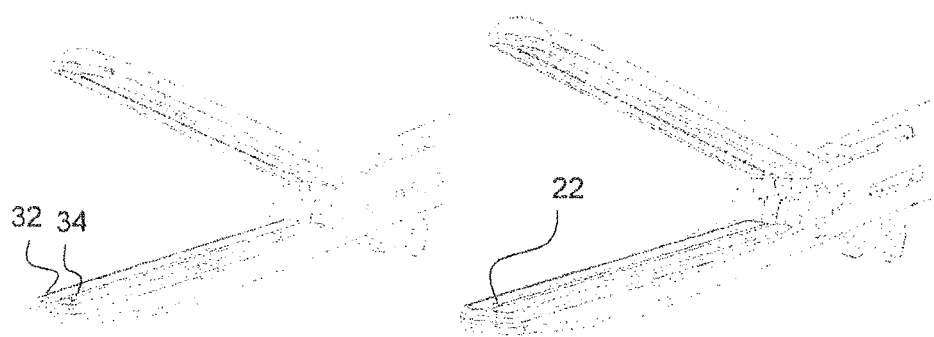
FIG. 15 shows a perspective view of two mutually pivotable instrument legs of an electrosurgical instrument according to a fifth embodiment of the invention.
FIG. 16 shows an electrosurgical instrument according to a sixth embodiment of the invention.

FIG. 15 shows a perspective view of the (opened) jaw part according to the fifth embodiment, from which it can be taken that the distal spacer is formed by two (nub-shaped) protrusions 32, 34 on the electrode areas 20-3 and 20-4 of the lower instrument leg 6 (fixed), as in the second embodiment.

FIG. 16 shows the (opened jaw part) according to a sixth embodiment of the invention, which differs from the laparoscopic electrosurgical instrument 2 of the fifth embodiment only in the arrangement of the distal spacer(s). As in the first embodiment, the distal spacer is implemented as a (nub-shaped) protrusion 22 arranged between the electrode areas 20-3 and 20-4 of the lower instrument leg 6. In other respects, the sixth embodiment is equal to the fifth embodiment described above.

Figure 17:
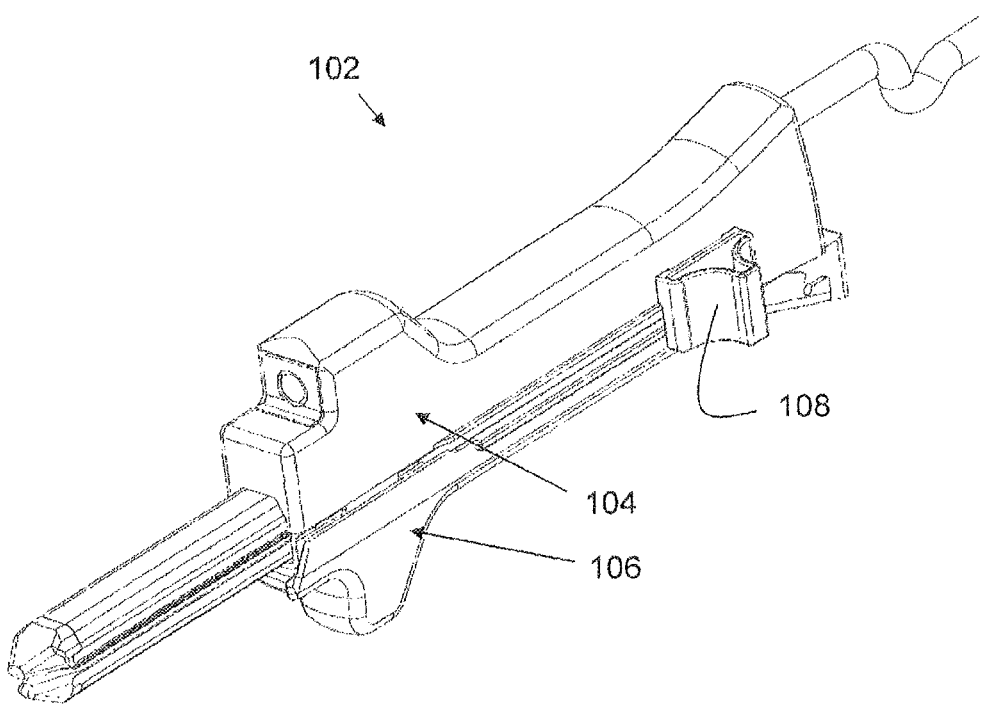
FIG. 17 shows an electrosurgical instrument according to a seventh embodiment of the invention.

FIG. 17 shows an electrosurgical instrument 102 according to a seventh embodiment, which differs from the instrument 2 described above in terms of the instrument type, in particular with regard to the construction of the operating device as well as the handle. Whereas all of the various embodiments described above have been described with reference to the laparoscopic electrosurgical instrument 2 illustrated in FIG. 1 comprising a thin, long shaft 12 and instrument legs 4 and 6 pivotally articulated thereon as a distal jaw part, the variants of the spacer arrangement which have been described above can also be realized in connection with the instrument 102 in which, however, two instrument legs 104 and 106 are connected to each other via a slide element 108 and a corresponding operation mechanism (not shown in further detail). With this arrangement, the handle or handle piece comprises a kind of accommodation duct from which the instrument legs protrude in axial as well as distal manner. This duct is dimensioned such that the instrument legs are compressed by the duct when they are retracted via the slide element 108 into the duct. If the slide element 108 is again pushed toward the duct opening, the instrument legs move out of the duct and open in this process, preferably automatically due to a spring-type pre-loading means, for example.

At this point it is to be noted that the present invention is not limited to the embodiments described above. Various modifications are possible within the scope of protection of the appended claims.

To give an example, instead of the protrusion 36 on the electrode area 20-2, the third embodiment may use a spacer module like in the first or second embodiment as the proximal spacer.

Further, it is possible to arrange the protrusions or ridges on other electrode areas in all of the embodiments, as long as at most one protrusion is applied (fixed) on each electrode area according to the present, preferred exemplary embodiment.

The shape and size of the spacers may also be varied, as long as all spacers are adapted to one another such that the distance between the electrode areas is always the same at all points. Thus, the spacer may have the shape of pyramids, truncated pyramids, cylinders or cubes. Finally, the spacer module can be divided into two individual modules which are arranged side by side and have only one material tongue each.

In the following, a spacer 300 as well as a spacer abutment surface 350 will be described in more detail on the basis of FIGS. 18 to 20, as they are basically used in all preceding exemplary embodiments of a jaw part preferably on the electrode.

As already set forth, the spacers or protrusions 300 according to the present invention are formed from an electrically conductive material (i.e. electroconductive) and preferably integrally connected to an associated electrode 360 which is shown exemplarily. The corresponding protrusion 300 can be formed by a corresponding stamping and bending process or by (locally) embossing/pressing the electrode 360 itself. In principle, there is also the option to fix the electrically conductive protrusion 300 for instance in the shape of a cone according to FIGS. 18 to 20 or a hemisphere on the electrode 360 by welding, soldering or forming. In each case, this allows to achieve a high strength between the protrusion 300 and the electrode 360 as well as a protrusion with intrinsic rigidity, so that any unintentional scraping or breaking off the protrusion formed in this way is avoided to the greatest possible extent.

Plate-shaped or disc-shaped recesses or indentations 372 are formed on the opposing electrode 370 (of the respective other leg) in the region of the protrusion 300. These indentations 372 further comprise a central blind hole or through hole 374 in the electrode 370, which extends in the direction of the thickness of the electrode 370. In this way, a kind of mushroom-shaped recess is produced in the respective electrode 370, as seen in the longitudinal section according to FIGS. 18 to 20.

A pin, pad or plug 350 made of an electrically non-conductive material is inserted in said indentation, whose shape is substantially exactly matched with the indentation and defines the spacer abutment surface. As an alternative to this, it is also possible to inject a potting compound made of an electrically non-conductive material into the indentation, which hardens afterwards.

Figure 18:
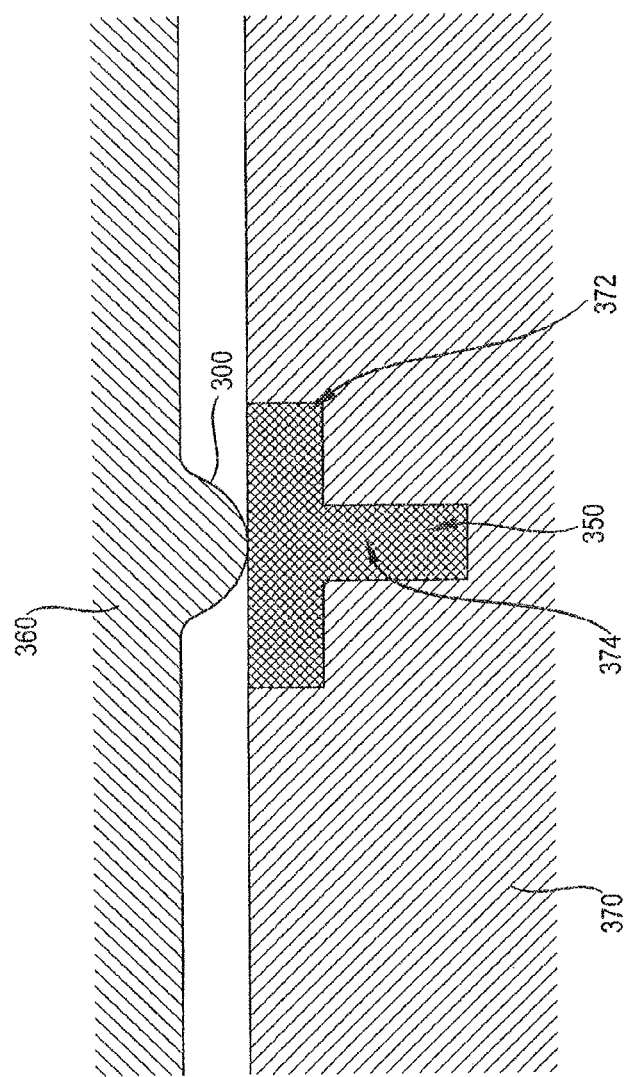
FIG. 18 shows a detail view of a spacer as well as a spacer abutment surface according to a first exemplary embodiment of the invention.

According to FIG. 18, the plug 350 is substantially flush or level with the surface of the corresponding electrode 370. In this way, the plug 350 does not constitute any external point of attack in terms of being pulled out of the indentation. In addition, the outer surface of the plug 350 is adapted substantially to the opposing protrusion 300 and is only of such a size that the protrusion 300, during pressing the two legs against each other, rests on the plug 350 in reliable manner without any direct contact with the respective electrode.

Figure 19:
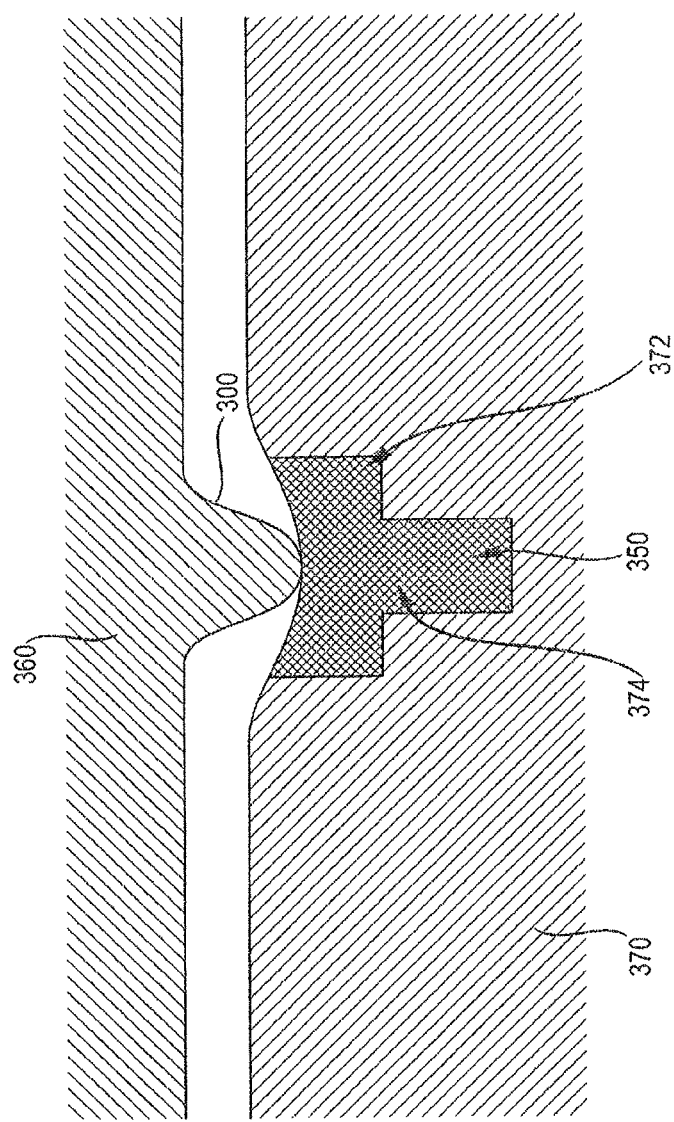
FIG. 19 shows a detail view of a spacer as well as a spacer abutment surface according to a second exemplary embodiment of the invention and FIG. 20 shows a detail view of a spacer as well as a spacer abutment surface according to a third exemplary embodiment of the invention.
Figure 20:
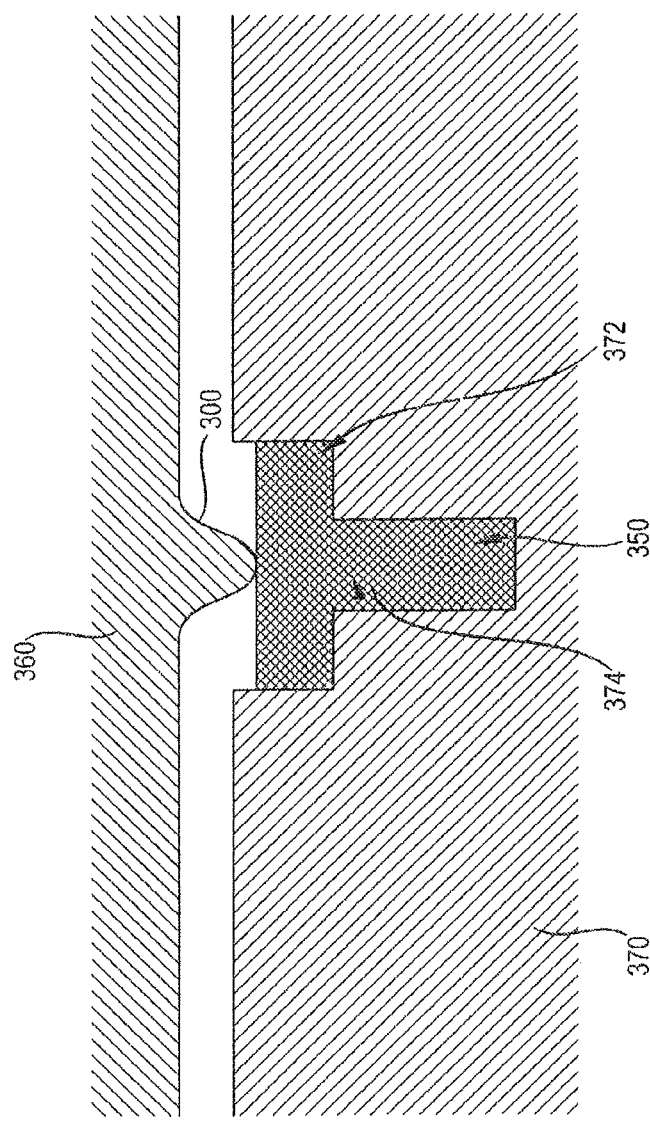

FIGS. 19 and 20 each show alternative configurations for the plug 350 (spacer abutment surface); according to FIG. 19, a concave outer surface is provided on the plug 350, bringing about a better centering of the opposing protrusion 300 when the legs are pressed against each other; according to FIG. 20, the plug 350 is (slightly) recessed with respect to the surface of the corresponding electrode, so as to avoid a protruding portion in any case.

Finally, it is to be pointed out that the spacer abutment surface basically may also have a shape which differs from that of the plug 350 which is shown. Thus, it is possible to design the spacer abutment surface exclusively with a flat shape, i.e. as a platelet. It is also possible to give the plug 350 the shape of a pyramid or cone. Candidates for the material of the spacer abutment surface are ceramics or synthetic materials. It is also possible to provide an intermediate layer between the spacer abutment surface (in particular the plug 350) and the electrode 370; said intermediate layer would compensate for any thermally induced, different material expansions of the electrode 370 and the spacer abutment surface and in this way prevent the spacer abutment surface from breaking or oozing out of the recess 372.

The invention claimed is:

1. An electrosurgical instrument comprising a jaw part made up of mutually movable instrument legs or branches which have facing sides on which one or more electrode surfaces are either arranged or formed in each case, the movement of the instrument legs or branches relative to each other being limited by at least one first spacer acting on proximal end portions of the instrument legs or branches and at least one second spacer acting on distal end portions of the instrument legs or branches, wherein at least one of the spacers on at least one electrode comprises an electrically conductive material and is connected to the electrode in electroconductive fashion, and cooperates with a local spacer abutment surface which comprises a non-conductive material and is arranged in electrically insulating manner on at least one opposing electrode, wherein the spacer abutment surface comprises a concavity which points toward the spacer or is recessed with respect to the electrode area.

2. The electrosurgical instrument according to claim 1, wherein the spacer abutment surface comprises a pad-shaped or pin-shaped component whose areal width on an electrode plane protrudes beyond the spacer on all sides, so that the spacer does not come into electrical contact with the electrode comprising the spacer abutment surface.

3. The electrosurgical instrument according to claim 2, wherein the electrode comprising the spacer abutment surface is formed to have at least one indentation on its surface, in which the spacer abutment surface in the form of a pad or pin is inserted, or which is cast with an electrically insulating material which forms the spacer abutment surface after solidification.

4. The electrosurgical instrument according to claim 3, wherein the indentation is mushroom-shaped or T-shaped as seen in longitudinal section.

5. The electrosurgical instrument according to claim 1, wherein at most one protrusion acting as an electrically conductive spacer is either provided or fixed on each of the electrode surfaces.

6. The electrosurgical instrument according to claim 1, wherein at least one spacer is a spacer module which is formed separate from the instrument legs or branches and comprises at least one electrically non-conductive material tongue which is clamped between the instrument legs or branches in a closed position, a height (H) of the material tongue corresponding to a predetermined minimum distance (S) between the instrument legs or branches in the closed position.

7. The electrosurgical instrument according to claim 6, wherein the spacer module is rotatably supported in a swivel joint of a first instrument leg or branch, which is pivotable, and is enclosed by flange-shaped joint portions of the pivotable instrument leg or branch, which define an accommodation cavity for the spacer module.

8. The electrosurgical instrument according to claim 1, wherein at most one protrusion acting as a spacer is either provided or fixed on each of the electrode areas, at least one spacer being a spacer module which is formed to be separate from the instrument legs or branches and comprises at least one electrically non-conductive material tongue which is clamped between the instrument legs or branches in a closed position, a height (H) of the material tongue corresponding to a predetermined minimum distance (S) between the instrument legs or branches in the closed position, and the spacer module being rotatably supported in a swivel joint of a first instrument leg or branch, which is pivotable, and being enclosed by flange-shaped joint portions of the pivotable first instrument leg or branch, which define an accommodation cavity for the spacer module.

9. The electrosurgical instrument according to claim 8, wherein the first instrument leg or branch is pivotally guided at its proximal end portion in a mounting opening of a second instrument leg or branch or a carrier part thereof, by said first instrument leg or branch having its proximal end portion enclosed by the second instrument leg or branch or the carrier part at diametric sides; and the accommodation cavity of the spacer module being formed in the first instrument leg or branch, which is pivotally guided, in such a way that the flange-shaped joint portions of said pivotally guided first instrument leg or branch come to lie between the spacer module and the second instrument leg or branch.

10. The electrosurgical instrument according to claim 8, wherein a spacer is formed by a protrusion which is arranged on a distal end portion of a second instrument leg or branch between two electrode areas of said second instrument leg or branch and points toward the first instrument leg or branch, or a spacer that is formed by a protrusion provided on an electrode area or by several protrusions each provided on different electrode areas.

11. The electrosurgical instrument according to claim 8, wherein at least one third spacer which acts on middle portions of the instrument legs or branches, said third spacer being formed as a protrusion and being arranged such that the number of spacers which are either arranged or fixed on one electrode area does not exceed the value 1.

12. The electrosurgical instrument according to claim 8, wherein between the proximal end portion and the distal end portion of at least one instrument leg or branch, one or more ridges pointing toward the respective other instrument leg or branch are formed at regular intervals, said ridges having a height (H) which is less than the height (H) of the spacers and amounts to between 10% and 75% of the height (H) of the spacers, the protrusions and/or the ridges and/or at least the material tongue of the separate spacer module comprising an electrically non-conductive material.

13. The electrosurgical instrument according to claim 1, wherein the spacers are arranged exclusively outside of a region provided for tissue treatment.

14. The electrosurgical instrument according to claim 1, wherein at least one of the instrument legs or branches comprises a rotation limiter pin which is guided in a slot-type guide on the side of the respective other instrument leg or branch, the cooperation between the rotation limiter pin and the slot-type guide establishing or simulating a spacer, and the instrument legs or branches having a predetermined minimum distance (S) relative to each other if the rotation limiter pin reaches an end of the slot-type guide.

15. The electrosurgical instrument according to claim 1, wherein between the proximal end portion and the distal end portion of at least one instrument leg or branch, one or more ridges pointing toward the respective other instrument leg or branch are formed at regular intervals, said ridges having a height (h) which is less than a height (H) of the spacers and amounts to between 10% and 75% of the height (H) of the spacers.

* * * * *